United States Patent [19]

Brode, II et al.

[11] Patent Number: 4,837,005
[45] Date of Patent: Jun. 6, 1989

[54] PARTIALLY HYDROLYZED, POLY(N-ACYL)ALKYLENIMINES IN PERSONAL CARE

[75] Inventors: George L. Brode, II, Bridgewater, N.J.; Frederick M. Merritt, II, Lockport, Ill.

[73] Assignee: Union Carbide Corporation, Danbury, Conn.

[21] Appl. No.: 913,407

[22] Filed: Sep. 30, 1986

[51] Int. Cl.$^4$ .................. A61K 7/00; A61K 7/021; A61K 7/06; A61K 7/45
[52] U.S. Cl. ..................... 424/47; 252/DIG. 13; 252/117; 252/547; 424/78; 424/71; 424/63; 424/65; 424/70; 424/72; 424/73
[58] Field of Search ............. 424/78, 65, 47, 70, 424/73, 71, 72, 63; 525/410; 252/DIG. 13, 117, 547

[56] References Cited

U.S. PATENT DOCUMENTS

| | | | |
|---|---|---|---|
| 3,579,630 | 5/1971 | Herz et al. | 424/47 |
| 3,833,521 | 9/1974 | Karbstein et al. | 525/417 |
| 3,862,310 | 1/1975 | Quasius | 424/78 X |
| 4,104,228 | 8/1978 | Meyer et al. | 525/410 X |
| 4,161,581 | 7/1979 | Wagner et al. | 525/411 |
| 4,190,644 | 2/1980 | Green et al. | 424/70 |
| 4,492,788 | 1/1985 | Cooke | 525/410 |

FOREIGN PATENT DOCUMENTS 1720436 2/1968 Fed. Rep. of Germany.
1720437 2/1968 Fed. Rep. of Germany.

*Primary Examiner*—Thurman K. Page
*Assistant Examiner*—Susan S. Rucker
*Attorney, Agent, or Firm*—Henry H. Gibson

[57] ABSTRACT

Partially hydrolyzed, poly(N-acyl)alkylenimines), and novel nitrogen-substituted derivatives thereof, provide useful and improved personal care compositions and processes.

19 Claims, No Drawings

PARTIALLY HYDROLYZED, POLY(N-ACYL)ALKYLENIMINES IN PERSONAL CARE

BACKGROUND OF THE INVENTION

1. Field Of The Invention

This invention relates to poly(N-acyl alkylenimines) in personal care, and more particularly to partially hydrolyzed, poly(N-acyl alkylenimines), and to nitrogen-substituted derivatives thereof, and to personal care compositions and processes using such polymers.

2. Descrption Of Background Information

Various cationic polymeric components used in personal care provide desirable managing characteristics when applied to keratinous substrates. For example, cationic celluloses have been found to exhibit superior conditioning and substantivity to keratinous substrates, as well as other properties significant for personal care utility. Various cationic cellulosics, however, provide limited solubility in nonaqueous systems and provide limited stability under certain pH conditions, consequently limiting their applicability to certain personal care applications. Cationic polyvinyl pyrrolidones exhibit good solubility but are relatively limited in conditioning ability with respect to the conditioning ability provided by existing cationic celluloses. Copolymers of acrylamide and dimethyl, diallyl ammonium chloride also provide utility in personal care including good solubility, but can contain residual monomers deleterous in personal care applications.

Poly(N-acyl alkylenimines) have been used in personal care applications. U.S. Pat. No. 3,579,630 (Herz et al.) discloses hair dressing formulations with poly(N-acyl ethylenimine) homoand copolymers. The poly(N-acyl alkylenimines) described in the Herz et al. patent are nonionic polymers, and as such do not provide significant substantivity to keratinous substrates thereby limiting their utility in personal care applications.

Various poly(alkylenimines), and processes for producing such polymers, are disclosed in U.S. Pat. No. 3,833,521 (Karbstein et al.), U.S. Pat. No. 4,161,581, (Wagner et al.), U.S. Pat. No. 4,492,788 (Cooke), West German Published Patent Application No. 1,720,436 (Seeiger et al. I) and West German Published Patent Application No. 1,720,437 (Seeliger et al. II).

There is a need, however, for a class of polymers having utility in personal care which exhibit both substantivity and flexibility in combination with a desirable balance of additional properties useful in personal care applications. It would also be desirable if such a class of polymers provide additional utility including: solubility in water and other hydrophilic solvents; film strength and gloss; moisture retention; low solution viscosity; as well as additional properties enabling widespread utility in a variety of personal care applications.

SUMMARY OF THE INVENTION

Personal care compositions are provided comprising carrier and an effective managing amount of partially hydrolyzed poly(N/acyl alkylenimine). The poly(N-acyl alkylenimine) contains repeating units represented by the structural formula:

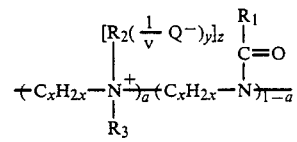

wherein a is form about 1 to about 50 mole percent. For each repeating unit individually, in this formula: Q is an anion; $R_1$ is hydrogen, alkyl, aryl, alkaryl or aralkyl; $R_2$ is hydrogen or a hydrocarbyl-containing group; $R_3$ is hydrogen, oxygen or a hydrocarbyl-containing group; v is equal to the valence of Q; x is 2 or 3; and y is 0 or 1; and z is 0 or 1; with the provisos that: (1) when $R_3$ is oxygen and y is 0, $R_2$ is a hydrocarbyl-containing group and z is 1; and (2) when $R_3$ is not oxygen then y is 1.

A process for producing such compositions is provided which comprises providing carrier with an effective managing amount of such poly(N-acyl alkylenimine).

A process for managing keratinous substrate is also provided which comprises applying an effective managing amount of such poly(N-acyl alkylenimine) to the sbustrate.

Nitrogen substituted, partially hydrolyzed, poly(N-acyl alkylenimines) are also provided which have the structural formula and parameters of the previous formula with the further provisos that:

(1) when all $R_2$ and $R_3$ groups are hydrogen then the average value of z per repeating unit is greater than 0 and Q represents a mixture of anions; and (2) when all z values are 0 then at least one $R_3$ group is a hydrocarbyl-containing group.

DETAILED DESCRIPTION OF THE INVENTION

The partially hydrolyzed, poly(N-acyl alkylenimines) of this invention provide significant and improved utility in personal care applications. The partially hydrolyzed, poly(N-acyl alkylenimines) of this invention can be tailored to provide desirable: solution viscosities; solubilities in water and other hydrophilic solvents; compatibilty with a broad spectrum of surfactants; substantivity; equilibrium moisture content; stability; film-forming properties; low toxicity and/or other performance characteristics, making such polymers eminently suitable in a wide variety of personal care applications.

Partially hydrolyzed, poly(N-acyl alkylenimines) of this invention are prepared by the partial hydrolysis of poly(N-acyl alkylenimine) precursors containing repeating units represented by the structural formula:

(I)

wherein n is at least about 200, and most preferably from about 500 to about 200,000, and most preferably from about 2,000 to 10,000.

In formula I, for each repeating unit individually, the $R_1$ group in the acyl substituent is hydrogen, alkyl, aryl, aralkyl or alkaryl group. The $R_1$ group will generally have form one to about 12 carbon atoms. Suitable $R_1$ groups include, but are not limited to: methyl, ethyl, n-propyl, isopropyl, n-butyl, isobutyl, t-butyl, n-dodecyl, benzyl, phenyl, methylphenyl, and the like. The $R_1$ group is preferably hydrogen or a linear or branched, saturated, aliphatic alkyl group containing from one to about 3 carbon atoms, and is most preferably ethyl.

In Formula I, for each repeating unit individually, the extent of the alkylene group, defined by x, is 2 or 3, and is most preferably 2.

The poly(N-acyl alkylenimines) precursors, as well as partially hydrolyzed or nitrogen-substituted derivatives thereof, possess terminal groups, not shown in the formulas. These terminal groups are not critical and generally are the residue groups normally provided during polymerization while producing the poly(N-acyl alkylenimine) precursors, or which may be provided by terminal group substitution, following established procedures. Typically, poly(N-acyl alkylenimine) terminal groups include, but are not limited to, hydrogen, hydrocarbyl, halogen and terminal groups as provided in U.S. Pat. No. 4,161,581 and the references cited therein.

A particularly preferred poly(N-acyl alkylenimine) precursor is poly(N-propionyl ethylenimine), for when $R_1$ is ethyl and x is 2, which contains repeating units represented by the structural formula:

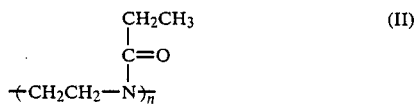

(II)

wherein n is as defined previously.

The poly(N-acyl alkylenimine) precursors are commercially available or may be derived by the polymerization of oxazolines. Such polymerization procedures are well established in the art, such as described in U.S. Pat. No. 3,579,630 (Herz et al.) and U.S. Pat. No. 4,492,788 (Cooke).

The hydrolyzing agent used to hydrolyze the poly(N-acyl alkylenimines) precursor may be either an acid or base, and is preferably an acid. The hydrolyzing agent may be any acid or base having sufficient strength to effect partial hydrolysis of the poly(N-acyl alkylenimine) precursor under appropriate hydrolyzing conditions.

Suitable hydrolyzing agents include, but are not limited to: mineral acids, such as sulfuric acid, sulfonic acid, hydrochloric acid, hydrobromic acid, phosphoric acid, nitric acid, and the like or mixtures thereof; bases such as sodium hydroxide, potassium hydroxide, and the like or mixtures thereof; and other known hydrolyzing agents or mixtures thereof.

Preferred hydrolyzing agents include: hydrochloric acid, phosphoric acid, sulfuric acid, and most preferably, concentrated hydrochloric acid.

The hydrolysis reaction is generally conducted in the presence of a suitable solvent capable of providing a reaction medium for the poly(N-acyl alkylenimine) precursor and hydrolyzing agent. Typical solvents include, but are not limited to, aqueous solutions; i.e., having water as solvent; organic solvents, such as ethanol; and other known solvents; or mixtures thereof.

The amount of poly(N-acyl alkylenimine) precursor provided in a reaction medium for hydrolysis is not critical. Generally, the concentration of poly(N-acyl alkylenimine) precursor will range from about 5 to about 50, preferably from about 10 to about 40, and most preferably from about 20 to about 30 weight percent of the total weight of the reaction mixture.

The amount of hydrolyzing agent provided is not critical so long as an effective hydrolyzing amount is provided sufficient to partially hydrolyze the poly(N-acyl alkylenimine) precursor. The amount of hydrolyzing agent may be stoichiometrically equivalent to or greater than the desired extent of hydrolysis.

The relative proportion of hydrolyzing agent to poly(N-acyl alkylenimine) precursor is not critical so long as sufficient hydrolyzing agent is provided to effect partial hydrolysis of the poly(N-acyl alkylenimine) precursor. Generally, the amount of hydrolyzing agent provided will range from about 0.05 to about 1, preferably from about 0.08 to about 0.5, and most preferably from about 0.1 to about 0.3 moles per mole of poly(N-acyl alkylenimine) repeat units.

Optional adjuvants may be provided to the reaction mixture, generally after hydrolysis, following procedures well established in the art. Typical adjuvants include: stabilizers; biocides, such as methylparaben; buffers; and other known adjuvants.

The hydrolysis reaction is conducted under conditions sufficient to effect partial hydrolysis of the poly(N-acyl alkylenimine) precursor. Hydrolysis may be achieved following procedures well established in the art, such as described in U.S. Pat. No. 4,492,788 (Cooke) and West German Published Patent Application No. 1,720,437 (Seeliger et al. II).

The particular process conditions and steps for conducting the hydrolysis reaction of this invention are not critical so long as they are sufficient to effect partial hydrolysis.

The hydrolysis temperature will typically range from about 80° C., to about 160° C., preferably from about 90° C. to about 120° C., and most preferably from about 100° C. to about 110° C. The hydrolysis pressure may be at, above or below atmospheric pressure, and is generally at least atomspheric, preferably from atmospheric to about 500 psig, and is most preferably from atmospheric up to about 20 psig.

The time required for conducting the partial hydrolysis will vary depending upon the particular poly(N-acyl alkylenimine) precursor and concentration thereof, the particular hydrolyzing agent and concentration thereof, and various process conditions. Generally, the partial hydrolysis will take at least about 2 hours, preferably from about 6 hours to about 20 hours, and most preferably from about 8 hours to about 12 hours.

Once the desired degree of partial hydrolysis is achieved the partially hydrolyzed, poly(N-acyl alkylenimine) product is recovered, including using known recovery procedures, the procedures described in this application, or both.

Partially hydrolyzed, poly(N-acyl alkylenimine) produced in any form may be purified, concentrated, otherwise treated or untreated, using well established procedures, to recover the desired form of partially hydrolyzed, poly(N-acyl alkylenimine) product.

If heat is used to assist the hydrolysis process, the product solution may be cooled to ambient temperature prior to recovery. Alternatively, the product solution may be adjusted to a combination of high basicity and high temperature sufficient to provide a precipitate of free amine of the partially hydrolyzed, poly(N-acyl alkylenimine). This precipitate may be separated from the solution to provide purified, partially hydrolyzed, poly(N-acyl alkylenimine) in the free amine form as a solid, or when cooled as a liquid.

Recovery of the partially hydrolyzed, poly(N-acyl alkylenimine) as a mixed quaternary ammonium salt may be achieved by neutralizing the product solution. When the hydrolyzing agent is an acid the neutralizing agent would be a base, and correspondingly when the hydrolyzing agent is a base the neutralizing agent would be an acid. Typical and preferred neutralizing agents include the hydrolyzing agents listed previously and other known hydrolysis neutralizing agents. Mixed quaternary ammonium salts of poly(N-acyl alkyenimine) may be recovered directly after neutralization while in solution without additional purification steps.

Partially hydrolyzed, poly(N-acyl alkylenimine) polymer so produced contains repeating units representing the structural formula:

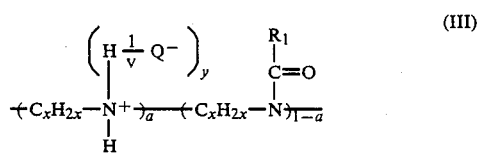

(III)

The proportion of hydrolyzed alkylenimine repeating units in the partially hydrolyzed, poly(N-acyl alkylenimine) of Formula III, defined by a, is generally from about 1 to about 50, preferably from about 3 to about 30, and most preferably from about 5 to about 20 mole percent.

In Formula III, substituents defined by the parameters, Q, v and y may be the same for each repeating unit throughout the polymer or may be different from the corresponding substituent in other repeating units. For each repeating unit individually in Formula III the parameters are defined as follows.

Quaternary ammonium salts of the partially hydrolyzed, poly(N-acyl alkylenimines) of Formula III are provided when Q groups are present, i.e., when y is 1. Q is an anion, including mono-or divalent organic or inorganic anions. Suitable anions include, but are not limited to, one or more of the following: organic anions such as carboxylates including propionate, butyrate, formate, benzoate and the like; inorganic anions such as halides including chloride, bromide and iodide; sulfonates; sulfates; phosphites; phosphates; phosphonates; carbonates; nitrates; and the like. Particularly preferred anions include chloride, proprionate and mixtures thereof. The Q anionic group may be provided by an acid hydrolyzing, or acid neutralizing, agent or by the hydrolyzed acylate group. Anionic groups may also be provided by an ion exchange mechanism or other known processes.

The N-acyl substituent of the partially hydrolyzed, poly(N-acyl alkylenimines) of Formula III, defined by $R_1$, is the same, generally and preferably, as the $R_1$ group defined previously for the poly(N-acyl alkylenimine) precursor of Formula I.

The valence of the anion Q of the partially hydrolyzed, poly(N-acyl alkylenimines) of Formula III, defined by v, determines the relative proportion of anion to quaternary ammonium cation, in inverse proportion. The value of v will typically be 1 or 2, and is preferably 1 thereby providing an equivalent molar amount of anion to quaternary ammonium cation. The average value of v per repeating unit containing anion may be greater than or equal to one for partially hydrolyzed, poly(N-acyl alkylenimines) containing a mixture of ions of different valences.

The length of the alkylene chain in the partially hydrolyzed, poly(N-acyl alkylenimines) of Formula III, defined by x, is the same as x as defined previously for the poly(N-acyl alkylenimines) precursor of Formula I.

The presence or absence of quaternization in the backbone of the partially hydrolyzed, poly(N-acyl alkylenimines) of Formula III is defined by y. When y is 0 free amine is provided. When y is 1 quaternary ammonium, cationic nitrogen is provided. When all values of y are 0 the totally free amine form of partially hydrolyzed, poly(N-acyl alkylenimines) is provided. When all values of y are 1 the fully quaternized form of partially hydrolized, poly(N-acyl alkylenimine) is provided. When the average value of y per repeating unit is greater than 0 and less than 1 both free amine and quaternary ammonium nitrogen atoms are provided within the polymer.

Following neutralization the partially hydrolyzed, poly(N-acyl alkylenimine) will generally contained salt by-product. The level of salt contained in the product may be calculated as ranging from about 1 to about 20, and is preferably up to about 7 weight percent of the total product obtained in solution. Such salt can be retained or be removed by purification procedures well established in the art.

In a typical embodiment, the hydrolysis procedure involves either of two procedures. In a first procedure the hydrolysis involves: (a) dissolving the poly(N-acyl alkylenimine) precursor in water, or other solvent, at the desired weight percent; (b) heating the solution to the desired reaction temperature; (c) adding the acidic hydrolyzing agent; (d) holding the reaction temperature for a specified period of time; (e) cooling to below about 60° C.; (f) neutralizing to pH 6.5-7.0 with aqueous alkaline solution; (g) clarifying the solution; (h) generally adding preservative to thereby yield the desired concentration of partially hydrolyzed, poly(N-acyl alkylenimine) as a mixed quaternary ammonium salt in solution. In a second procedure the hydrolysis involves using the previously identified steps (a) through (d) for hydrolysis followed by: (e') causticizing to above pH 10 with aqueous alkaline solution, at or slightly below the reaction temperature; (f') separating the solid and liquid phases; (g') cooling to below about 60° C., (h') diluting the solution to the desired polymer concentration; (i') clarifying the solution; (j') generally adding preservative; to thereby yield the partially hydrolyzed, poly(N-acyl alkylenimine) in a free amine form having a reduced level of impurities.

Derivatives of partially hydrolyzed, poly(N-acyl alkylenimines) are provided by reacting the hydrolyzed, free amine present in the partially hydrolyzed, poly(N-acyl alkylenimine) of Formula III, with or wihtou some quaternary ammonium substitution present, to provide oxygen or hydrocarbyl-containing substituents on the hydrolyzed nitrogen. Such partially hydrolyzed, poly(N-acyl alkylenimines) derivative will contain repeat units represented by the structural formula:

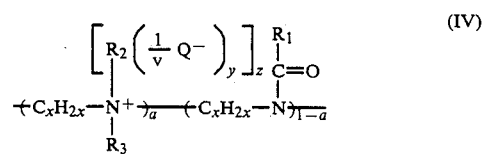

(IV)

wherein A, Q, $R_1$, v, x, and y are defined in Formula III. Some or all of the hydrogen on the nitrogen substituent will be replaced with (1) oxygen, as one or more $R_3$ groups; (2) hydrocarbyl-containing groups as one or more $R_2$ or $R_3$ groups, or both; or (3) both (1) and (2).

Derivatized nitrogen substituents, defined by $R_2$ and $R_3$ in Formula IV, are provided when the hydrogen substituents on the nitrogen atom are replaced with oxygen or any hydrocarbyl-containing group. Suitable hydrocarbyl-containing groups include, but are not limited to: alkyl, aryl, aralkyl, alkaryl, or alkyloxy groups containing one or more carbon atoms. Such hydrocarbyl-containing groups may be: linear, branched, or cyclic; saturated, unsaturated, or aromatic; and unsubstituted or substituted with functional groups such as hydroxyl, amino, ammonio, carboxyl, carboxylate, sulfonate, other known functional groups, or mixtures thereof. The derivatized nitrogen substituents may contain ionic groups providing the partially hydrolyzed, poly(N-acyl alkylenimine) derivatives with other ionic substitution, providing dicationic or amphoteric poly(N-acyl alkylenimine) derivatives when hydrolyzed nitrogen in the polymer backbone is present in the quaternized form.

In Formula Iv, the presence or absence of the $R_2$ group as well as of quaternization in the backbone of the partially hydrolyzed, poly(N-acyl alkylenimines) derivatives, defined by z, depends upon the type of derivatization present. When $R_3$ is oxygen the y is 0, $R_2$ is hydrocarbyl-containing group and z is 1. When $R_3$ is not oxygen then y is 1. When all $R_2$ and $R_3$ groups are hydrogen then the average value of z per repeat unit is greater than 0 and Q represents a mixture of anions, i.e., more than one type of anion is provided per polymer molecule. When all z values are 0 then at least one $R_3$ group in the nitrogen-substituted, partially hydrolyzed, poly(N-acyl alkylenimine) is a hydrocarbyl-containing group.

Oxidized derivatives of partially hydrolyzed, poly(N-acyl alkylenimines) contain repeating units represented by the structural formula:

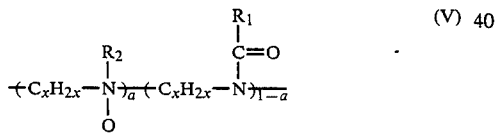

(V)

wherein a, $R_1$ and x are as defined in Formula III and, for each repeating unit individually, $R_2$ is a hydrocarbyl-containing group as defined for $R_2$ in Formula IV.

Partially hydrolyzed, poly(N-acyl alkylenimine) of Formula IV having tertiary amine hydrolyzed nitrogen, i.e., where $R_2$ is hydrocarbyl-containing, can be oxidized to the corresponding amine oxide derivative, defined by Formula V, i.e., where $R_3$ is oxygen, at one or more hydrolyzed nitrogen, using any known amine oxidizing agent following established procedures. Suitable oxidizing agents include, but are not limited to: acyl-, aryl- or alkyl-containing hydroperoxides or peroxides; hydrogen peroxide; ozone; or mixtures thereof. Preferred oxidizing agents include: hydrogen peroxide and other common oxidizing agents.

Any derivatization capable of providing a suitable nitrogen substituent containing a hydrocarbyl group can be conducted. Such derivatization reactions include, but are not limited to: alkylation, including the use of substituted or unsubstituted, hydrocarbyl halides, halohydrins, epoxides or other known alkylating agents; acylation, including the use of substituted or unsubstituted, acyl halides, esters, acid anhydrides, oxazolines, caprolactams or other known acylating agents; sulphonation, including the use of substituted or unsubstituted sulphonyl halides or other known sulphonating agents; carbamoylation, including the use of haloformates or other known carbamoylating agents; formation of ureas and thioureas, including the use of isocyanates, isothiocyanates or other known (thio)urea forming agents; and other amine derivatization reactions, including mixtures of such agents.

Typical derivatization include, but are not limited to, the following reactions.

The partially hydrolyzed, poly(N-acyl alkylenimine) of Formula III may be derivatized by alkylation by reacting the hydrolyzed nitrogen with, for example, an alkyl-containing halide or epoxide to provide nitrogen substitution wherein: $R_2$, $R_3$ or both are alkyl-containing groups, y is one, and Q is a halide. For example, reaction of the polymer with halohydrins or 1,2 epoxides provides hydroxy substituted, nitrogen substituents. Suitable alkylating agents include, but are not limited to one or more of the following: halohydrins such as 3-chloro-2-hydroxypropyl trimethyl ammonium chloride, 3-chloro-2-hydroxypropyl dimethyldodecyl ammonium chloride, 3-chloro-2-hydroxypropyl dimethyloctadecyl ammonium chloride, 3-chloro-2-hydroxypropyl- dimethyloctyl ammonium chloride, and the like; and their corresponding 1-2 epoxides such as 2,3-epoxypropyl trimethyl ammonium chloride, and the like; halohydrin sulfonates such as monochlorohydrin sulfonate; and other alkylating agents for secondary amines known in the art. Preferred alkylating agents include: 3-chloro-2-hydroxypropyltrimethyl ammonium chloride, 3-chloro-2-hydroxypropyl dimethyldodecyl ammonium chloride, 3-chloro-2-hydroxypropyl dimethyltetradecyl ammonium chloride, 3-chloro-2-hydroxypropyl dimethylhexadecyl ammonium chloride, 3-chloro-2-hydroxypropyl dimethyloctadecyl ammonium chloride, monochlorohydrin sulfonate and the like.

The partially hydrolyzed, poly(N-acyl alkylenimine) of Formula III may also be derivatized by suitable reaction of the polymer with heterocyclic compounds such as oxazoline, caprolactam, other known heterocyclic compounds, or mixtures thereof, to provide nitrogen-substitution containing a substituent primary amine. The derivatives containing such pendant nitrogen substituents can undergo further derivatization reactions of the substituent primary amine, following established procedures.

The partially hydrolyzed, poly(N-acyl alkylenimine) may also be derivatized through crosslinking by providing a crosslinker reactive with the hydrolyzed nitrogen. The crosslinker may be any suitable polyfunctional compound which reacts with the hydrolyzed nitrogen amine of the unsubstituted or nitrogen-substituted, partially hydrolyzed, poly(N-acyl alkylenimine). The crosslinker may be represented by the structural formula:

$$R\text{—}(z)_m \qquad (VI)$$

wherein m is at least 2, and preferably from 2 to 6.

In Formula VI, R is a polyvalent, substituted or unsubstituted, alkyl, cycloalkyl, aryl, alkaryl or aralkyl containing group having at least 1, preferably from about 2 to about 15 carbon atoms. Such R groups can be unsubstituted hydrocarbyl-containing groups or may contain hetero atoms. Suitable R groups include, but are not limited to, one or more of the following: heterocyclics, such as substituted triazines including hexamethylol melamine residues, ureas including bis(N,N-hydroxymethyl, methyl)urea residues; or other heterocyclics; alkylenes, such as methylene, ethylene, propylenes, 2-hydroxy-propylenes, cycloakylenes, such as cyclohexylenes; alkarylenes, such as 2,2-bis(p-hydroxyphenyl) propane, xylylenes; and the like. Preferred R groups include: 2,2-bis(p-hydroxyphenyl) propane, methylene and 2-hydroxypropylene.

In Formula VI, each z is individually a functional group which is reactive with the hydrolyzed nitrogen of the partially hydrolyzed, poly(N-acyl alkylenimine). Suitable z groups include, but are not limited to: halides such as chloride, bromide and the like; isocyanates; epoxides; aldehydes; carboxylic groups; hydroxy or alkoxy methyl groups; other known groups reactive with amines; and suitable mixtures thereof.

Suitable crosslinkers include, but are not limited to: dicarboxylic acids such as malonic, phthalic and oxalic; epichlorohydrin; dihaloalkanols such as dichloropropanol; methylene bis formamide; bisisocyanates such as m-tolylene diisocyanate, isophorone diisocyanate; aldehydes such as formaldehyde, glutaraldehyde; diepoxides such as butadiene diepoxide, diglycidyl ether of Bisphenol-A; other known crosslinkers; and mixtures thereof. Typical crosslinkers include those crosslinking agents disclosed in U.S. Pat. No. 3,640,909 (Jones et al.).

Crosslinked, partially hydrolyzed, poly(n-acyl alkylenimine) derivatives will contain from 1 up to m-1 $R_3$ groups, as defined previously, and contain repeating units represented by the structural formula:

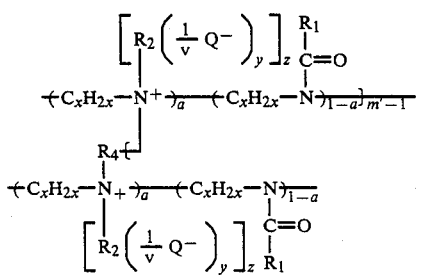

(VII)

wherein: a, Q, $R_1$, $R_2$, v, x, y and z are as previously defined in Formula IV and m' is from 2 to m as previously defined in Formula VI. The crosslinking group, defined by $R_4$ in Formula VII, is a polyvalent hydrocarbyl-containing group which is the residue of the crosslinker of Formula VI.

The amount of derivatizing agent provided is not critical but will vary depending upon the desired extent of derivatization. Typically, the amount of derivatizing agent will be from about 0.01 to about 10, preferably from about 0.5 to about 6, and most preferably from about 0.01 to about 1 moles per mole of hydrolyzed nitrogen in the poly(N-acyl alkylenimine).

The molecular weight of the partially hydrolyzed, poly(N-acyl alkylenimine) of Formula III, or derivatives thereof of Formula IV, is not critical by depends on the molecular weight of the poly(N-anyl alkylenimine) precursor, the extent of partial hydrolysis, as well as the degree and type of any derivatization. Generally, the partially hydrolyzed, poly(N-acyl alkylenimines), or derivatives thereof, of this invention will have a weight average molecular weight of at least about 10,000, preferably from about 30,000 to about 20,000,000, and most preferably from about 150,000 to about 1,500,000.

In a typical embodiment, the derivatization procedure involves: providing either in-situ generation of partially hydrolyzed, poly(N-acyl alkylenimine) or dissolution of pre-purified partially hydrolyzed, poly(N-acyl alkylenimine) at the desired concentration in the reaction solvent; adding the derivatizing agent; adjusting the reaction pH to about 10; and heating to reaction temperature of 60°–80° C. for a period of about 5 hours, to obtain the derivatized, partially hydrolyzed, poly(N-acyl alkylenimine) in solution.

Particular preferred partially hydrolyzed, poly(N-acyl alkylenimines), and derivatives thereof, provided by poly(N-acyl alkylenimine) precursors of Formula I when R is ethyl and z is 2, contain repeating units represented by the structural formula:

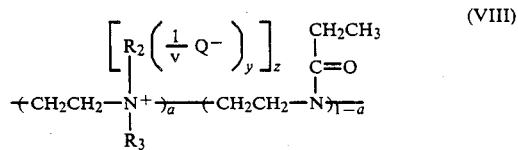

(VIII)

wherein a, Q, $R_2$, $R_3$, v, y and z are as defined in Formulas III or IV previously.

The personal care compositions of this invention comprise, and preferably consist essentially of, carrier, an effective managing amount of partially hydrolyzed, poly(N-acyl alkylenimine), and optionally effective amounts of other personal care ingredients.

Carrier, including mixtures of carriers, used in the personal care compositions of this invention act as a fluid vehicle for the partially hydrolyzed, poly(N-acyl alkylenimine) or derivative thereof, and other optional personal care ingredients. Such carriers may be any carrier selected from those well established in the personal care art. Illustrative examples of carriers include, but are not limited to: water, such as deionized or distilled water; alcohols, such as ethanol, isopropanol or the like; glycols, such as propylene glycol, glycerine or the like; and mixtures thereof. Preferred carrier systems include oil-in-water emulsions, water, ethanol and aqueous ethanol mixtures.

When the carrier is an aqueous solution, the pH may be varied over a wide range depending upon the particular personal care application, based on those procedures well established in the art. Under acidic and neutral conditions, the partially hydrolyzed, poly(N-acyl alkylenimine) or derivative thereof may be provided predominantly in the quaternary ammonium form; whereas under basic conditions the partially hydrolyzed, poly(N-acyl alkylenimine) or derivative thereof may be provided predominantly or essentially in the free amine form.

The amount of poly(N-acyl alkylenimine) polymer provided in the personal care composition of this invention is an effective managing amount, which is defined as that amount of polymer sufficient to provide effective or improved personal care utility to the composition.

In quantitative terms, the effective managing amount of polymer will vary depending upon the particular personal care application and extent of managing properties desired. In general, an effective managing amount of polymer will range between about 0.01 and about 25, preferably from about 0.1 to about 5, and most preferably from about 0.25 to about 2.5, weight percent of the total weight of the personal care composition.

The personal care compositions of this invention may optionally contain suitable ingredients or additives typical of personal care compositions, following well established practices in the art. Illustrative ingredients which may be suitable may include, but are not limited to, the following, including mixtures thereof. Illustrative surfactants may include: anionics such as fatty acid soaps, alkyl sulfates, alkyl ether sulfates, alkyl aryl sulfonates, sarcosinates and preferably sodium lauryl sulfate, ammonium lauryl sulfate, triethanol amine lauryl sulfate, sodium laureth sulfate, triethanol amine stearate and glycerol monostearate; nonionics such as fatty acid alkanol amides, alkyl aryl polyglycol ether, polyglycol ethers and preferably cocamide DEA, nonoxynol-7 and octoxynol-9; cationics such as alkyl trimethyl ammonium salts, quaternized amides of ethylene diamine, alkyl pyridinium salts and preferably cetrimonium chloride, stearalkonium chloride and cetyl pyridinium chloride; and amphoterics such as alkyl ö-aminopropionates, betaines, alkyl imidazolines and preferably cocamidopropyl betaine and caproamphocarboxypropionate. Illustrative cleansers may includee natural oils and alcohols and preferably mineral oil, lanolin oil, ethanol and isopropanol. Illustrative colorants may include pigments, dyes, and preferably FD&C Blue No. 1, FD&C No. 1 Aluminum Lake or similar sets of green, red or yellow. Illustrative preservatives may include alcohols, aldehydes, p-hydroxybenzoates and preferably methylparaben, propylparaben, glutaraldehyde and ethyl alcohol. Illustrative moisturizers may include fatty alcohols, fatty esters, glycols and perferably isopropyl myristate, lanolin or cetyl alcohols, propylene gylcol, glycerol and sorbitol. Illustrative pH adjustors may include inorganic and organic acids and bases and preferably aqueous ammonia, citric acid, phosphoric acid, acetic acid, triethanolamine and sodium hydroxide. Illustrative emulsifiers may include anionic and nonionic surfactants and preferably stearic acid, glycerol monostearate, cocoyl diethanolamide, and the preferred anionic and nonionic surfactants listed previously. Illustrative propellants may include hydrocarbons, fluorocarbons, ethers, carbon dioxide, nitrogent and dimethyl ether. Illustrative reducing agents may include ammonium thioglycolate and sodium thioglycolate. Illustrative conditioners may include homo- and copolymers of dialkyldimethyl ammonium chloride and acrylamide, copolymers of quaternized dimethyl aminoethyl acrylate and methacrylate with vinyl pyrrolidone and acrylamide, quaternary nitrogen-containing cellulose ethers, and preferably polyquaternium-10, polyquaternium-6 and polyquaternium-11. Illustrative thickeners may include sodium chloride, hydroxyethyl cellulose hydroxypropyl methyl cellulose, sodium carboxymethyl cellulose, guar gum and derivatives thereof, xanthan gum and derivatives thereof and polymers containing hydrophobe bunches including hydrophobe modified polyurethanes or other such polymers described in U.S. Pat. No. 4,426,485.

Other typical ingredients may include, but are not limited to, the following: fragrances; foaming agents; sunscreen and suntan agents; depilatory agents; flavors; astringent agents; antiseptics; deodorants; antiperspirants; insect repellants; bleaches and lighteners; antidandruff agents; adhesives; polishes; strengtheners for hair, nails, or the like; fillers; barrier materials; and other known personal care additives. Mixtures of such ingredients may also be provided.

The amount of ingredient contained in the personal care compositions of this invention is not critical but will vary depending upon the particular ingredient, composition and desired use level and can be any effective amount for achieving the desired property provided by such ingredients, following well established procedures known to those in the personal care art.

The personal care compositions of this invention are produced by providing an effective managing amount of partially hydrolyzed, poly(N-acyl alkylenimine), or derivatives thereof, along with optional personal care additives, such as any one or more of the ingredients previously described, to a suitable carrier. Typically, the polymer and other personal care additives may be admixed in the carrier to provide a personal care composition, following well established procedures.

The personal care compositions of this invention are used by applying an effective managing amount of the personal care composition to the hair, skin, teeth or other similar personal care substrate following those techniques well established in the personal care art. In a preferred embodiment, a process for managing keratinous substrates, such as hair or skin, is provided by applying an effective managing amount of personal care composition containing partially hydrolyzed, poly(N-acyl alkylenimine) to the keratinous substrate.

Illustrative personal care uses of this invention include, but are not limited to, the following: skin creams including cleansing, night, massage, moisturizing, vanishing, foundation, hand, hand/and-body, all-purpose creams and other known skin creams; astringents and skin tonics, including compositions for irritated, inflamed, allergic, hypersensitive or sensitized skin; protective creams and hand cleansers; bath preparations including foam baths, bath salts, bath oils, after-bath products, and other known bath preparations; baby skin and hair products; adolescent skin products, such as for oily skin or acne, and other adolescent skin products; antiperspirants and deodorants; depilatories; shaving preparations including wet shaving creams, sticks, foams, dry shaving lotions, powder, after-shave lotions, foams, aerosols, gels, creams, balms and powders, and other known shaving preparations; foot preparations including foot powders, sprays, creams, corn, callus and chilblain and atheletes's foot preparations and other known foot preparations; insect repellants; sunscreen, suntan and anti-sunburn preparation; skin lighteners or bleaches; face packs or masks including wax-, rubber-, vinyl-, hydrocolloid- or earth-based systems, anti-wrinkle preparations and other known face packs or masks; perfumes; face powders and make-up; colored make-up preparations including lipstick, lip salves, rouge, eye make-up such as mascara, eye shadow, eye liner and other known make-up preparation; shampoos including clear liquids, liquid creams or lotions, solid creams or gels, oils, powders, aerosols, dry, conditioning, baby, anti-dnadruff and medicated, acid-balanced shampoos and other known shampoos; hair setting preparations including lotions, sprays, dressings, brilliantines, fixatives, aerosols, emulsions, gels, and other known hair preparations; hair tonics and conditioners including rinses; hair colorants including temporary, semi-permanent, permanent or other hair dyes or colorants, hair dye removers, bleaches, lighteners and other known hair colorants; permanent wave and hair strengtheners; hair straighteners including caustic preparations, chemical hair reducing preparations and other known hair straighteners; dental products including dentifrices such as tooth paste, tooth gels, tooth powders, solid dentifrice, denture cleansers, adhesives, and other known dental products; mouth washes; and other known personal care compositions.

The novel, partially hydrolyzed, poly(n-acyl alkylenimines), and derivatives thereof, of this invention may be useful in applications other than personal care, such as flocculants, additives in paper manufacture, or other areas which known poly(N-acyl alkylanimines) provide utility.

The following examples are presented as illustrative embodiments of this invention and are not included to limit the scope thereof. Unless stated otherwise all percentages are given in weight percent.

EXAMPLES

The various designations used in the examples are defined as follows:

| Designation | Description |
| --- | --- |
| SB-85 | An aqueous solution of stearalkonium chloride, at 85 wt. % active concentration, identified as BARQUAT ® SB-85 by Lonza, Inc. |
| CHPDLACl | 3-chloro-2-hydroxypropyldimethyllauryl ammonium chloride. |
| CHPTACl | 3-chloro-2-hydroxypropyltrimethyl ammonium chloride. |
| EDTA | Trisodium salt of ethylenediaminetetraacetic acid. |
| EPTACl | 2,3-epoxypropyltrimethyl ammonium chloride. |
| ES-225 | A half ethyl ester of maleic anhydride/vinyl methyl ether copolymer, identified as GANTREZ ® ES-225 by GAF Corp. |
| GAF 937 | A copolymer of vinyl pyrrolidene and dimethyl aminoethyl methacrylate, identified as GAF ® 937 by GAF Corp. |
| HEC | A hydroxyethyl cellulose having a degree of substitution of about 2.0. |
| $H_{MW}$QNHEC | Quaternary-nitrogen containing hydroxyethyl cellulose derivatized with 3-chloro-2-hydroxypropyltrimethyl ammonium chloride, having a 2 wt. % Brookfield viscosity of 456 cps and about 1.8 wt. % nitrogen. |
| $L_{MW}$QNHEC | Quaternary-nitrogen containing hydroxyethyl cellulose derivatized with 3-chloro-2-hydroxypropyltrimethyl ammonium chloride, having a 2 wt. % Brookfield viscosity of 125 cps and about 1.8 wt. % nitrogen. |
| MCHS | Monochlorohydrin sulfonate. |
| PEG-60 Lanolin | A 60 mole ethoxylate of lanolin, identified as Solan ® brand by Croda. |
| PPEI(20M) | Homopolymer of N—propionyl ethylenimine having a weight average molecular weight of 20,000, identified as Poly(ethyloxazoline) XAS-10874.01 by Dow Chemical Co. |
| PPEI(200M) | Homopolymer of N—propionyl ethylenimine having a weight average molecular weight of 200,000, identified as Poly(ethyloxazoline) XAS-10874.03 by Dow Chemical Co. |
| PPEI(500M) | Homopolymer of N—propionyl ethylenimine having a weight average molecular weight of 500,000, identified as Poly(ethyloxazoline) XAS-10874.05 by Dow Chemical Co. |
| RH | Relative humidity. |
| ES-2 | A sodium laureth sulfate, identified as STANDAPOL ® ES-2 by Henkel Corp. |
| STEARETH-20 | A polyethylene glycol ether of stearyl alcohol, identified as STEARETH ®-20 by ICI Americas. |
| TEALS | Triethanolamine lauryl sulfate. |
| TWEEN ® 20 | A polysorbate mixture of laurate esters, identified as TWEEN ® 20 by ICI Americas. |

Polymer Characterization Procedures

Unless otherwise indicated, the following test procedures for polymer characterization are used in the examples.

Ash Analysis: The average weight percent of component is determined by elemental analysis using standard ashing procedures measured relative to the dry polymer.

DS: The degree of substitution is the average mole percent of the substituted nitrogen determined by the numerical average of the mole percent values using the following three procedures:

Potentiometric Titration; the average mole percent hydrolysis, based on millipores of propionic acid, is determined analytically by standard titration procedures, factoring out the contribution of amine hydrochloride substitution.

Chloride content, % Cl; the average weight percent of chloride is determined analytically using standard Ash Analysis procedures as described previously.

Nitrogen content, % N; the average weight percent of nitrogen is determined analytically by standard Kjeldahl procedures.

Viscosity: viscosity is measured using Brookfield LVT viscometers, based on an aqueous solution of 2 wt. % designated polymer at 25° C.

Performance Testing Procedures

Unless otherwise indicate, the following testing procedures are used to measure various properties of the poly(N-acyl alkylenimines) which are significant in indicating personal care utility. Where specified, treated hair tresses are provided using a two gram, 10-inch tress of commercially available virgin brown hair. One milliliter of a 1 wt. % solution of designated polymer in water solvent, with or without surfactant is applied to the tress manually.

Appearance: Hair treated with poly(N-acyl alkylenimines) is rated on a scale of from 1 to 5, with 5 as the highest rating, with respect to wet and dry sheen, dry flakiness and other known appearance properties.

Combability: Wet and dry combability is measured by combing a treated hair tress and measuring how far the comb travels before it is stopped by tangles. Tresses which are 10 inches in length, i.e., 23 centimeters, provide a maximum value of 23.

Curl Retention: This test measures the ability of the poly(N-acyl akylenimines) to hold a hair sample in a curl after the polymer is applied and the curl rolled. The test measures the rate and extent of relaxation of a curl formed by a hair roller as follows. The polymer is applied manually and not by spray to facilitate a more uniform application of the polymer to the hair. The test is conducted under constant temperature and humidity conditions and measures the loss of curl over time. The treated hair tresses are wound around and clipped to a 2 by 7 centimeter roller, with commercial end paper.

The rolled tress is dried for about an hour and then brought to the constant temperature and humidity test conditions over about an hour. The tress is slid gently from the roller, the end paper is removed and the horizontal length of the curl measured. The test is begun by hanging the curl in air and continues by monitoring the change in the length over time. Mesurements are taken at 15 minute intervals for 1 hour. Data is recorded as percent curl retention, calculated from the following relationship:

$$\% \text{ Curl Retention} = \frac{L_I - L_T}{L_I - L_C} \times 100$$

wherein:

$L_I$ is the initial length of the tress;
$L_C$ is the initial length of the curl; and
$L_T$ is the length of the curl at specified time.

The rate of loss of curl retention is obtained using linear regression analysis of the linear equation obtained by plotting the natural logarithm of curl retention as a function of time.

Feel: Hair tresses, produced as described in the Examples, are evaluated, on a scale of 1 to 5 with 5 as the highest rating, with respect to greasiness, stickiness, dryness, softness, slip and other standard performance properties.

Fly-away: This test measures the diameter of the hair tress after rapidly combing the tress 10 times. Superior performance is provided by lower values.

Gloss: This test measures the glossiness, using a Gardiner glossimeter at ambient conditions, of films of the specified polymer cast on the bottom of wax coated cups, at 20° and 60° angles of incidence.

Moisture Retention: This test measures the ability of polymer to retain water, providing an indication of humectancy in personal care. The test procedure involves dessicating polymer in a vacuum oven at approximately 50° C. The dried polymer is placed in an enclosed chamber over a saturated salt solution and the amount of water uptake in the polymer is measured, based on increased weight. The percent moisture obtained at a specified relative humidity is measured after exposure at ambient temperature for 138 hours.

Solubility: Specified weight percent solutions of designated poly(N-acyl alkylenimines) in various solvents are measured with respect to solubility of the polymer in such solutions.

Sprayability: This test measures the ability of the specified solution of designated poly(N-acyl alkylenimines) to provide a spray, using a pump or aerosol procedure. Sample mists are measured, on a scale of 1 to 10 with 10 as the highest rating, with respect to spray pattern, fineness of spray, area coverage, drying rate and droplet formation characteristics.

Viscosity Stability: This test measures the storage stability of designated poly(N-acyl alkylenimines) solutions to retain viscosity in time. The specified weight percent polymer solutions are produced and stored for three months. The viscosity of such solutions is measured, at specified times, using the previously described procedure.

EXAMPLES 1-15:

Partial Hydrolysis of Poly(N-acyl alkylenimines)

These Examples illustrate various procedures for preparing and recovering partially hydrolyzed, poly(N-acyl alkylenimines) used in this invention.

EXAMPLE 1

A 2-liter reaction flask is equipped with a mechanical stirrer, reflux condenser, thermometer, dropping funnel, and oil bath with automatic control. Deionized water, 912 g, is added and 96 g of PPEI (200M) is added in one portion and stirred until dissolved. The reactor is closed and heated to reflux in 58 minutes; the polymer clouds out of solution above about 75° C. Concentrated HCl, 48.5 g, is added from the dropping funnel in 20 seconds, and the reflux is continued for 90 minutes; the polymer dissolves in the reaction medium at about 40-50 minutes. The reaction is cooled to 28° C. in 12 minutes and a sample is pulled for analysis of the degree of hydrolysis by gas chromatography. The reaction medium is neutralized to pH 6.6 with 20.5 weight percent NaOH, the water is removed under a vacuum, the solids are dissolved in anhydrous ethanol, the solution is filtered, the ethanol is removed under vacuum, and the solid product is dried in a 50° C. vacuum oven for 48 hours. Product analysis is set forth in Table I.

EXAMPLE 2

The procedure in Example 1 is repeated except the PPEI(200M) is replaced with 96 g of PPEI(20M). Product analysis is set forth in Table I.

EXAMPLE 3

The procedure in Example 1 is repeated except that the PPEI(200M) is replaced with 96 g of PPEI(500M). Product analysis is set forth in Table I.

EXAMPLE 4

A 2-liter reaction flask is equipped with a mechanical stirrer, reflux condenser, thermometer, dropping funnel, and oil bath with automatic control. Distilled water, 912 g, is added and 96 g of PPEI(200M) added in one portion and stirred until dissolved. The reactor is closed and heated to reflux in 50 minutes; the polymer clouds out of solution above 76°. Concentrated HCl, 48.5 g, is added in 45 seconds and reflux is continued for 90 minutes; the polymer dissolves in the reaction medium at about 40 minutes. The reaction is cooled to 28° C. in 10 minutes and a sample is taken for hydrolysis analysis. The solution is treated with enough Amberlite ®900 resin in the hydroxide form to a pH of 11.5, the resin is filtered, and the product is isolated by rotoevaporation and freeze drying. Product analysis is set forth in Table I.

EXAMPLE 5

A stirred Parr reactor, Model 4522 made of monel alloy, is equipped with a dip tube, cooling coils, nitrogen source, and sampling cylinder. PPEI(200M), 95 g, is predissolved in 938.3 g of distilled water and transferred to the reactor. Concentrated HCl, 11.72 g, is added with swirling, the reactor is sealed, and the stirrer motor and coolant is started. The reactor is heated to 120° C. in 25 minutes and 45 psig is generated. Samples are pulled for hydrolysis analysis via the sampling cylinder at one hour intervals. The reactor is rapidly cooled after 5.92 hours reaction, opened, and 20.9 g of 20.07% sodium hydroxide is added to adjust the solution pH to 6.87. The product is isolated by roto-evaporation and freeze drying to give a crisp, greenish-colored solid. The green color comes from Cu and Ni salts due to corrosion of the Monel stirrer. Product analysis is set forth in Table I.

EXAMPLE 6

A 250 ml 3-necked flask is equipped with a mechanical teflon stirrer, thermometer, condenser, oil bath, and dropping funnel. Anhydrous 2B ethanol, 105.4 g, is charged and 12 g PPEI(200M) is dissolved with stirring. The solution is heated to reflux (80° C.) in 45 minutes and 14.6 g of concentrated HCl is added in 20 seconds. The reaction is allowed to continue for 2 hours and quickly cooled to ambient, and a sample is taken for hydrolysis analysis. The mixture is treated with 20.07% sodium hydroxide to a pH of 6.8. The product is isolated by roto-evaporation and analyzed with the results set forth in Table I.

EXAMPLE 7

The same reaction apparatus as described in Example 1 is used. Deionized water, 1672 g, is added and 169.5 g of PPEI (200M) is added over several minutes and dissolved with stirring. The reactor is closed and heated to reflux in 30 minutes; the polymer clouds out of solution above about 75° C. Concentrated HCl, 20.8 g, is added from the dropping funnel and reflux is maintained for a total of 17 hours, at which time the polymer is dissolved in the reaction medium. The reaction is cooled to 25° C. in 30 minutes and a sample is pulled for analysis of degree of hydrolysis by gas chromatography. The reaction medium is neutralized to pH of 6.8 by the addition of 47.9 g of 20.07 weight percent NaOH. The solid polymer is isolated by roto-evaporation and freeze drying. Product analysis is set forth in Table I.

EXAMPLE 8

The procedure in Example 7 is repeated except the hydrolysis is done for only 16 hours. Product analysis is set forth in Table I.

EXAMPLE 9

The procedure is Example 8 is repeated except the PPEI (200M) is replaced with 169.5 g of PPEI (500M). Product analysis is set forth in Table I.

EXAMPLE 10

The procedure in Example 8 is repeated except the reaction medium is overneutralized to pH 7.9 with 17.5 g of 50 weight percent NaOH and back-neutralized to pH 7.02 with concentrated HCl. The isolated product had a high salt content which was reduced by dissolving the solids in 90/10 w/w acetone/water at a 10 weight percent concentration, filtering, and removal of the ethanol by roto-evaporation. The residue was redissolved in water and freeze dried. Product analysis is set forth in Table I.

EXAMPLE 11

A 500 ml reaction flask is equipped with a mechanical stirrer, reflux condenser, thermometer, dropping funnel, and an oil bath with automatic control. Deionized water, 418 g, is added and 42.4 g of PPEI (200M) is added in one portion and dissolved with stirring. The reactor is closed and heated to reflux in 45 minutes. Concentrated HCl, 5.2 g, is added and the reflux is maintained for 16 hours. The reaction temperature is maintained between 95° C. and 98° C., while 19.95 g of 20.07 weight percent NaOH is slowly added to bring the reaction medium to pH 10.63; polymer begins clouding out at about 6.5 pH and is in solid form at the final pH. The liquid phase was removed with suction through a submerged filter. The concentrated polymer phase is cooled to ambient temperature to give a concentrated solution of product. Both the liquid effluent and the concentrated polymer solution are freeze dried to isolate solids. Product analysis is set forth in Table I.

EXAMPLE 12

The procedure in Example 11 is repeated except that the amount of deionized water is reduced to 401 g, the amount of concentrated HCl is increased to 21.3 g, and the hydrolysis reaction time is decreased to 90 minutes. A total of 63.15 g of 20.07 weight percent NaOH is added at about 98° C. to adjust the reaction pH to 11.05 and the liquid phase is removed by a submerged filter. Product analysis is set forth in Table I.

EXAMPLE 13

The procedure in Example 11 is repeated except that the amount of deionized water is reduced to 409 g, the amount of concentrated HCl is increased to 13.0 g, and the hydrolysis reaction time is decreased to 230 minutes. A total of 38.3 g of 20.07 weight percent NaOH is added at about 96°-98° C. to adjust the reaction pH to 10.50 and the liquid phase is removed by a submerged filter. Product analysis is set forth in Table I.

EXAMPLE 14

The procedure in Example 11 is repeated except that the amount of PPEI (200M) is increased to 92.84 g, the amount of deionized water decreased to 343 g, the amount of concentrated HCl is increased to 28.52 g, and the hydrolysis reaction time is decreased to 3 hours. A total of 101.2 g of 19.67 weight percent NaOH is added at about 97° C. to adjust the reaction pH to 10.7 and the liquid phase is removed by a submerged filter. Product analysis is set forth in Table I.

EXAMPLE 15

The procedure in Example 14 is repeated except that the PPEI (200M) is replaced with 92.84 g of PPEI (500M). Product analysis is set forth in Table I.

TABLE 1

PREPARATION OF PARTIALLY HYDROLYZED, POLY(N—ACYL ALKYLENIMINES)

| Example | Poly(N—acyl alkylenimine) Molecular Weight (× 1000) | Concentration | Reactant Mole Ratio[a] | Degree of Hydrolysis (mole %)[b] | Salt Level (calc wt. %)[c] |
|---|---|---|---|---|---|
| 1 | 200 | 9.1 | 0.495 | 11.6 | 3.95 |
| 2 | 20 | 9.1 | 0.495 | 11.3 | 7.52 |
| 3 | 500 | 9.1 | 0.495 | 13.2 | 2.55 |
| 4 | 200 | 9.1 | 0.495 | 13.0 | 3.10 |
| 5 | 200 | 9.1 | 0.12 | 11.0 | 7.37 |
| 6[d] | 200 | 9.1 | 1.19 | 2.3 | 13.29 |
| 7 | 200 | 9.1 | 0.12 | 11.5 | 7.24 |
| 8 | 200 | 9.1 | 0.12 | 12.1 | 7.20 |
| 9 | 500 | 9.1 | 0.12 | 12.5 | 7.65 |
| 10 | 200 | 9.1 | 0.12 | 13.0 | 6.83 |
| 11 | 200 | 9.1 | 0.12 | ND[e] | 1.99 |
| 12 | 200 | 9.1 | 0.50 | ND[e] | 3.55 |
| 13 | 200 | 20.0 | 0.30 | 11.3 | 3.07 |
| 14 | 200 | 20.0 | 0.30 | 13.0 | 9.07 |

TABLE 1-continued

PREPARATION OF PARTIALLY HYDROLYZED, POLY(N—ACYL ALKYLENIMINES)

| Example | Poly(N—acyl alkylenimine) Molecular Weight (× 1000) | Concentration | Reactant Mole Ratio[a] | Degree of Hydrolysis (mole %)[b] | Salt Level (calc wt. %)[c] |
|---|---|---|---|---|---|
| 15 | 500 | 20.0 | 0.30 | ND[e] | 9.31 |

[a]Moles of hydrolyzing agent per mole of poly(N—acyl alkylenimine) repeat units.
[b]Moles of hydrolyzed nitrogen measured per mole of nitrogen in poly(N—acyl alkylenimine), designated by parameter a in Formulas I and IV, times 100. Determined by gas chromatography, based on equivalent moles of propionic acid measured after hydrolysis.
[c]Calculated from average weight percent of sodium chloride using previously described Ash Analysts procedure.
[d]Using anhydrous ethanol as diluent, instead of water.
[e]Not determined.

EXAMPLES 16–26:

Preparation of Nitrogen-Substituted Derivatives of Partially Hydrolyzed, Poly(N-acyl Alkylenimines).

These examples illustrate procedures for preparing nitrogen-substituted derivatives of partially hydrolyzed, poly(N-acyl alkylenimines) as prepared in the previous Examples 1–15. In Examples 16–19, the nitrogen-substituent contains a cationic group providing a dicationic, nitrogen-substituted derivative of partially hydrolyzed, poly(N-acyl alkylenimine). In Examples 20–22, the nitrogen-substituent contains hydrophobic, cationic groups providing a hydrophobic, dicationic, nitrogen-substituted derivative of partially hydrolyzed, poly(N-acyl alkylenimine). In Examples 23 and 24, the nitrogen-substituent contains an anionic group providing an amphoteric, nitrogen-substituent derivative of partially hydrolyzed, poly(N-acyl alkylenimine). In Examples 25 and 26, the nitrogen-substituent contains a dihydroxy group providing a vicinal diol-containing, nitrogen-substituted derivative of partially hydrolyzed, poly(N-acyl alkylenimine).

EXAMPLE 16

A suitably sized 3-neck reaction flask is equipped with a mechanical stirrer, pH probe, and an oil bath with automatic control. Deionized water, 34.5 g, is added and 15.75 g of the polymer produced in Example 4 is added and dissolved with stirring. A 60 weight percent aqueous solution of 3-chloro-2-hydroxypropyl-trimethylammonium chloride, 6.39 g, is added and the pH is adjusted to 12.05 with 4.6 g of 20.26 weight percent NaOH. The mixture is heated to 65° C. for 310 minutes while adding small increments of the aqueous NaOH (an additional 0.2 g) to maintain the pH at about 10.5. The reaction is cooled and neutralized to a pH of 6.85 with concentrated HCl. After freeze drying and initial analysis, the product was dissolved in deionized water at a 10% concentration, dialyzed to remove impurities, and freeze dried. Product analysis is set forth in Table II.

EXAMPLE 17

The procedure in Example 16 is repeated except that the amount of deionized water is 75 g, the polymer of Example 4 is replaced with 18.71 g of the polymer prepared in Example 7, and 12.78 g of the 60% 3-chloro-2-hydroxypropyltrimethylammonium chloride is added. A total of 11.9 g of 20.07 weight percent NaOH is added to maintain the reaction pH. The reaction medium was purified by dialysis and the product isolated by freeze drying. Product analysis is set forth in Table II.

EXAMPLE 18

The procedure in Example 17 is repeated except the polymer of Example 7 is replaced with 17.93 g of the polymer prepared in Example 9. A total of 11.5 g of 20.07 weight percent NaOH is added to maintain the reaction pH. Product analysis is set forth in Table II.

EXAMPLE 19

A suitably sized 3-neck flask is equipped with a mechanical stirrer, a pH probe, and an oil bath with automatic control. Deionized water is added and 18.56 g of the polymer prepared in Example 7 is added and dissolved with stirring. A 70.54 weight percent aqueous solution of 2,3epoxypropyltrimethylammonium chloride, 4.3 g, is added and the pH is adjusted to 11.7 with 3.0 g of 20.07 weight percent NaOH. The reaction is heated to 65° C. and held for 300 minutes while maintaining the reaction pH at about 10.5 with an additional 0.1 g of the 20.07 weight percent NaOH. The reaction is cooled and the product purified by dialysis and freeze drying. Product analysis is set forth in Table II.

EXAMPLE 20

In the standard apparatus as in Example 19, 59 g of deionized water is added and 18.71 g of the polymer prepared in Example 7 is added and dissolved with stirring. A 42.97 weight percent aqueous solution of 3-chloro-2-hydroxypropyldimethyllaurylammonium chloride, 31.84 g, is added and the pH is adjusted to 10.6 with 10.2 g of 20.07 weight percent NaOH. The reaction is heated to 65° C. and held for 300 minutes; pH is kept at about 10.5 with an additional 1.0 g of the aqueous NaOH. The reaction is cooled and the somewhat viscous solution is diluted with 312 g deionized water and decanted. The residue is diluted with 300 g deionized water, centrifuged and decanted, dissolved in water, dialyzed, and freeze dried. Product analysis is set forth in Table II.

EXAMPLE 21

In the standard apparatus as in Example 19, 59 g of anhydrous 28 ethanol is added and 18.71 g of the polymer prepared as in Example 7 is added and dissolved with stirring. A 42.97 weight percent aqueous solution of 3-chloro-2-hydroxypropyldi -methyllaurylammonium chloride, 31.84 g, is added and the pH adjusted to 10.83 with 9.8 g of 20.07 weight percent NaOH. The reaction is heated to 80° C. for 300 minutes while maintaining the reaction pH with incremental additions of another 1.4 g of the aqueous NaOH. The reaction is cooled and the product is purified by dialysis and freeze drying. Product analysis is set forth in Table II.

EXAMPLE 22

The procedure in Example 11 is repeated except that the polymer of Example 7 is replaced with 17.93 g of the polymer prepared in Example 9. A total of 10.9 g of 20.07 weight percent NaOH is added to adjust and maintain the reaction pH. Product analysis is set forth in Table II.

EXAMPLE 23

In the standard apparatus as in Example 19, 25 g of deionized water is added and 16.8 g of the polymer prepared in Example 8 is added and dissolved with stirring. A 30 weight percent aqueous solution of monochlorohydrinsulfonate, 11.8 g, is added and the pH, is adjusted to 10.68 with 6.2 g of 20.07 weight percent NaOH. The reaction is heated to 65° C. for 300 minutes with no adjustment needed to maintain the pH. The reaction is cooled and the product is purified by dialysis and freeze drying. Product analysis is set forth in Table II.

EXAMPLE 24

The procedure in Example 23 is repeated except that the amount of deionized water is reduced to 67 g and the amount of 30 weight percent monochlorohydrinsulfonate is increased to 23.6 g. Addition of 9.8 g of 20.07 weight percent NaOH adjusts the reaction pH to 10.09. Product analysis is set forth in Table II.

EXAMPLE 25

Nitrogen substitution of the partially hydrolyzed, poly(N-acyl alkylenimine) produced in Example 10 is provided using the following procedure. In the standard apparatus as in Example 19, 150 g deionized water is added and 32.5 g of the polymer prepared in Example 10 is added and dissolved with stirring. Glycidol, 5.82 g, is added and the pH is adjusted to 10.6 with 6.8 g of 19.60 weight percent NaOH. The reaction is heated to 65° C. for 300 minutes, cooled, and the product purified by dialysis and freeze drying. Product analysis is set forth in Table II.

EXAMPLE 26

The procedure is Example 25 is repeated except the amount of glycidol is increased to 11.64 g and 7.0 g of the aqueous NaOH is used to obtain a reaction pH of 10.55. Product analysis is set forth in Table II.

TABLE 2

PREPARATION OF NITROGEN-SUBSTITUTED DERIVATIVES OF PARTIALLY HYDROLYZED, POLY(N—ACYL ALKYLENIMINES)

| Example | Polymer Example Number | Derivitizing Agent | Reactant Mole Ratio[a] | $DS^b$ (mole %) | Viscosity |
|---|---|---|---|---|---|
| 16 | 4 | CHPTACl | 1.0 | 5.9 | 32 |
| 17 | 7 | CHPTACl | 2.0 | 5.6 | 39 |
| 18 | 9 | CHPTACl | 2.0 | 5.3 | 31 |
| 19 | 7 | EPTACl | 1.0 | 4.6 | 36 |
| 20 | 7 | CHPDLACl | 2.0 | 7.7 | >2000 |
| 21[c] | 7 | CHPDLACl | 2.0 | 5.8 | 580 |
| 22[c] | 9 | CHPDLACl | 2.0 | 4.6 | 981 |
| 23 | 8 | MCHS | 1.0 | 6.4[d] | 32 |
| 24 | 8 | MCHS | 2.0 | 12.8[d] | 32 |
| 25 | 10 | Glycidol | 2.0 | 9.6[e] | 33 |
| 26 | 10 | Glycidol | 4.0 | 10.8[e] | 31 |

[a]Moles of derivatizing agent per mole of hydrolyzed nitrogen.
[b]Degree of Substitution, using previously described analysis procedures.
[c]Using anhydrous ethanol as reaction medium, instead of water.
[d]Calculated from weight percent sodium using previously described Ash Analysis procedure.
[e]Based on values from Potentiometric Titration procedure only, as previously described.

EXAMPLES 27-56 AND CONTROLS A-K:

Personal Care Evaluations

These examples illustrate various personal care compositions having partially hydrolyzed, poly(N-acyl alkylenimines) of this invention. In Example 27, the solubilities of various partially hydrolyzed, poly(N-acyl alkylenimines), or nitrogen-substituted derivatives thereof, are evaluated. In Examples 28-32, personal care compositions containing the designated concentrations of partially hydrolyzed, poly(N-acyl alkylenimines) are prepared by mixing together the listed ingredients. In Examples 33-35 and Controls A-B, hair spray formulations containing various partially hydrolyzed, poly(N-acyl alkylenimines) are analyzed and compared to commercially available polymers. In Examples 36-43 and Controls C-D the stability of various partially hydrolyzed, poly(N-acyl alkylenimine) solutions and formulations are evaluated. In Examples 44-48 and Controls E-H the film properties of various partially hydrolyzed, poly(N-acyl akylenimines) are analyzed and compared to commercially available polymers. In Examples 49-51 and Controls I-J the hygroscopicity of various partially hydrolyzed, poly(N-acyl alkylenimine) solutions and formulations is evaluated. In Examples 52-55 and Control K the substantivity of various partially hydrolyzed, poly(N-acyl alkylenimines) is evaluated. In Example 56 the toxicity of various partially hydrolyzed, poly(N-acyl alkylenimines) is evaluated.

EXAMPLE 27:

Solubility Analysis

This example demonstrates that partially hydrolyzed, poly(N-acyl alkylenimines), and nitrogen substituted derivatives thereof, are soluble in a wide variety of solvents.

Partially hydrolyzed, poly(N-propionyl alkylenimines) produced in Examples 1-3 provide complete solubility at 5 and 10 weight percent concentrations in propylene glycol and glycerin, as well as at 20 weight percent in water and anhydrous ethanol. Nitrogen-substituted cationic derivatives of partially hydrolyzed, poly(N-propionyl alkylenimines) produced in Examples 16-22 provide solubility in acetone and chloroform. Nitrogen substituted, hydrophobe modified, cationic derivatives of partially hydrolyzed poly(N-propionyl alkylenimines), produced in Examples 20-22, provide complete solubility in ethanol, acetone and chloroform.

Partially hydrolyzed, poly(N-acyl alkylenimines) are also soluble in aqueous solutions over a wide range of temperatures and pH. The partially hydrolyzed, poly(N-propionyl alkylenimine) produced in Example 4 is completely soluble at a pH of 1 up to 100° C., at a pH of 11.1 a cloud point in aqueous solution at 72°-76° C. is provided; and at a pH of 10.8 in ethanol no cloud point is exhibited up to reflux temperature of 80° C.

EXAMPLE 28:

Hand Lotions

Hand lotions containing the designated concentrations of poly(N-propionyl ethylenimines), produced in Examples 9 and 10 are prepared by combining the ingredients listed below using the following procedure:
Preparation procedure :
1. Heat the oil phase to 70° C.
2. In separate container, dissolve the polymer in water then add other water phase ingredients and heat to 70° C.
3. Add the water phase to the oil phase while stirring vigorously.
4. Continue stirring until the temperature of the lotion is 30°-35° C.
Oil phase:

| | |
|---|---|
| Mineral Oil (carrier) | 2.4 |
| Isopropyl myristate (emollient) | 2.4 |

-continued

| | |
|---|---|
| Stearic acid (thickener) | 2.9 |
| Lanolin alcohol (emulsifier) | 0.5 |
| Cetyl alcohol (thickener/stabilizer) | 0.4 |
| Glycerol monostearate (thickener/stabilizer) | 1.0 |
| Propyl paraben (preservative) | 0.05 |

Water phase:

| | |
|---|---|
| Triethanolamine (pH adjustor) | 0.95 |
| Propylene glycol (humectant) | 4.8 |
| Methyl paraben (preservative) | 0.1 |
| Polymer | 0, 0.25, 0.4, 0.5, 1.0 and 2.0 |
| Water (carrier) | to 100 |

Although some incompatibility is exhibited, the hand lotion formulations containing 0.25 and 0.4 weight percent polymer are stable for prolonged periods at ambient conditions. At 2 weight percent polymer concentrations the hand lotion formulations are stable at ambient temperature for several weeks. At 50° C. in an accelerated aging test analysis for 28 days, the hand lotion formulations containing 0.25 weight percent polymers are completely stable; at 0.4 weight percent polymers a slight loss in homogeneity is exhibited; whereas at 0.5 weight percent or higher polymer concentrations phase separation occurs overnight.

EXAMPLE 29
PERMANENT WAVE FORMULATIONS

Permanent wave compositions containing the designated concentrations of poly(N-propionyl ethylenimines), produced in Examples 8, 9 and 10, are prepared by combining the following ingredients:

| | |
|---|---|
| Ammonium thioglycolate (reducing agent) | 9.0 |
| EDTA (metal chelating agent) | 0.2 |
| Propylene glycol (humectant) | 2.5 |
| Aqueous ammonia (pH adjustor) | to pH 9-9.2 |
| Polymer | 0, 1 and 2 |
| Water (carrier) | to 100 |

EXAMPLE 30
AFTER SHAVE FORMULATIONS

After shave compositions containing the designated concentions of poly(N-propionyl ethylenimines), produced in Examples 8, 9 and 10, prepared by combining the following ingredients:

| | |
|---|---|
| Propylene glycol (humectant) | 0.5 |
| Polymer | 0, 1 and 2 |
| Anhydrous ethanol (2B) (carrier) | to 100 |

EXAMPLE 31
SHAMPOOS

Shampoos containing the designated concentrations of poly(N-propionyl ethylenimines), produced in Examples 9 and 10, are prepared by combining the following ingredients:

| | |
|---|---|
| TEALS (40% active) (surfactant) | 7.0 |
| Lauric diethanolamide (foam booster) | 2.0 |
| TWEEN ® 20 (fragrance stabilizer and emollient)) | 3.0 |
| STANDAPOL ® ES-2 (surfactant) | 5.0 |
| EDTA (metal chelating agent) | 0.1 |
| Methyl paraben (preservative) | 0.2 |
| Propyl paraben (preservative) | 0.1 |
| Polymer | 0, 1 and 2 |
| Water (carrier) | to 100 |

EXAMPLE 32
CONDITIONING CREMES

Conditioning creme rinse containing the designated concentrations of poly(N-propionyl ethylenimines), produced in Examples 9 and 10, are prepared by combining the ingredients listed below using the following procedures: Preparation Procedure:
1. Heat oil phase to 75° C.
2. Separately, dissolve polymer in available water and heat to 75° C.
3. Add oil phase to water phase while stirring vigorously.
4. Start cooling, continue stirring, and add ucarcide when temperature is 35°-40° C.
5. Continue stirring until cooled to 30 ° C. Oil Phase:

| | |
|---|---|
| Mineral oil (carrier) | 2.0 |
| SB-85 (conditioner) | 6.0 |
| Cetyl alcohol (thickener) | 1.25 |
| Glycerol monostearate (emulsifier) | 0.75 |

Water Phase:

| | |
|---|---|
| UCARCIDE ® 225 biocide (preservative) | 0.4 |
| Polymer | 0, 1 and 2 |
| Water (carrier) | to 100 |

EXAMPLES 33-35 AND CONTROLS A AND B
Hair Spray Analysis

Hair spray formulations containing 1.5 weight percent designated polymer, 49.25 weight percent deconized water and 49.25 weight percent ethanol are evaluated using the previously described performance testing procedures, with the results set forth in Table 3.

TABLE 3
HAIR SPRAY ANALYSIS DATA

| Example: | 33 | 34 | 35 | Control A | Control B |
|---|---|---|---|---|---|
| Polymer: | Ex. 1 | Ex. 2 | Ex. 3 | $H_{MW}$ QNHEC | ES-225 |
| Wet Tests: | | | | | |
| Combability | 19 | 16 | 21 | 16 | 23 |
| Feel | 5 | 5 | 5 | 5 | 5 |
| Appearance | 5 | 5 | 5 | 4 | 5 |
| Dry tests: | | | | | |
| Combability | 23 | 23 | 23 | 23 | 23 |
| Fly-away | 10.9 | 6.4 | 6.4 | 6.4 | 3.8 |
| Appearance | 4 | 5 | 5 | 5 | 5 |
| Curl retention[a]: | | | | | |
| at 50% RH % | 83 | 91 | 80 | 95 | 84 |
| Rate of loss[b] | 19 | 6 | 17 | 10 | 10 |
| at 95% RH % | 73 | 76 | — | — | —[c] |

TABLE 3-continued

| HAIR SPRAY ANALYSIS DATA | | | | | |
|---|---|---|---|---|---|
| Example: | 33 | 34 | 35 | Control A | Control B |
| Rate of loss[b] | 48 | 34 | — | — | — |
| Sprayability:[d] | | | | | |
| Pattern | 10 | 10 | 10 | — | — |
| Wetness | 10 | 10 | 10 | — | — |

[a] at 70° F. and designated humidity
[b] ΔLn curl retention/minute × 10⁴
[c] generally 60%
[d] For a 2 wt. % polymer solution in ethanol using a commercially available pump spray unit.

Two weight percent solutions of various partially hydrolyzed, poly(N-acyl alkylenimines) in ethanol also exhibit good sprayability both in terms of spray pattern, including fineness of spray and area coverage, and quick drying performance, using pressurized aerosol sprays with hydrocarbon propellant.

The partially hydrolyzed, poly(N-acyl alkylenimines) perform comparably, and in some respects including humidity resistance perform superior to, the commercial available control polymers.

EXAMPLE 36–43 AND CONTROLS C–D

STABILITY ANALYSIS

Two weight percent aqueous solutions of the partially hydrolyzed, poly(N-propionyl ethylenimines) produced in Examples 1 and 3 are prepared and adjusted to a pH of 3.0 using sulfuric acid. Viscosities of the resulting solutions, following the previously described procedure using a UL adaptor at 60 RPM, are measured at room temperature, of about 25° C., and at 40° C. The resulting measurements, taken over several weeks, are set forth in Table 4.

TABLE 4

| VISCOSITY STABILITY AT LOW PH OF 3.0 | | | | | | |
|---|---|---|---|---|---|---|
| Example | Temperature (°C.) | Viscosity (cps,) over time, in weeks | | | | |
| | | 0 | 1 | 2 | 3 | 4 |
| 36 | 25 | 6.1 | 6.4 | 6.1 | 6.2 | 6.0 |
| 37 | 40 | 6.1 | 6.3 | —[a] | 5.7 | 5.4 |
| 38 | 25 | 3.5 | 3.7 | 3.2 | 3.6 | 3.5 |
| 39 | 40 | 3.5 | 3.3 | 3.2 | 3.2 | 3.2 |

[a] not available

The results indicate that at an acidic pH solutions of partially hydrolyzed, poly(N-acyl alkylenimines) exhibit good storage stability. In constrast, solutions of cationic cellulosic materials are subject to acid hydrolysis thereby providing poor stability at low pH. The stability provided by partially hydrolyzed, poly(N-acyl alkylenimines) at acidic pH demonstrates the utility of such material in hair-care products, such as lower pH conditioners which impart better appearence to the hair due to a natural ability to cause the cuticle in the keratin to lay down closer to the hair shaft, thereby producing a glossier surface and resulting the increased hair manageability.

Stability at high pH is evaluated in cream formulations, specifically calcium hydroxide cream relaxer products, using partially hydrolyzed, poly(N-propionyl ethylenimines) produced in the Examples 1 and 5, as well as a control formulation of identical ingredients but without polymer, as follows:

| HIGH PH CREAM FORMULATIONS | |
|---|---|
| Ingredient | Amount (wt. %) |
| Polymer | 2 |
| Propylene glycol (humectant) | 5 |
| Petrolatum (texturizer) | 12 |
| Mineral oil (carrier) | 10 |
| Cetyl alcohol (thickener) | 8 |
| Steareth-20 (emulsifier) | 3 |
| PEG-60 lanolin (emulsifier) | 1.5 |
| Calcium hydroxide (pH adjustor) | 5.5 |
| Fragrance | 0.25 |
| Water (carrier) | to 100 |

The storage stability of these formulations, at room temperature of about 25° C. and at 40° C., are evaluated by measuring viscosity, separation or preciptation with the results set forth in Table 5.

TABLE 5

| STORAGE STABILITY AT HIGH PH (Ca(OH)₂ CREAM RELAXER) | | | | | | | | |
|---|---|---|---|---|---|---|---|---|
| Ex. | Polymer | Temperature (°C.) | Viscosity (10⁵ cps) over time, in weeks | | | | | Separation/ Precipitation |
| | | | 0 | 1 | 2 | 3 | 4 | |
| 40 | 1 | 25 | 4.368 | 4.368 | 4.1184 | 4.4928 | 4.68 | None |
| 41 | 1 | 40 | 4.368 | 5.304 | 4.992 | 5.304 | 5.2416 | None |
| 42 | 5 | 25 | 4.68 | 5.2416 | 4.8048 | 5.304 | 5.4288 | None |
| 43 | 5 | 40 | 4.68 | 6.24 | 5.6784 | 6.24 | 6.24 | None |
| C | None | 25 | 5.304 | 5.5536 | 5.2416 | 4.992 | 5.3664 | None |
| D | None | 40 | 5.304 | 6.1776 | 5.616 | 5.928 | 5.8302 | None |

The results demonstrate good storage stability for high pH formulations of poly(N-acyl alkylenimines) in typical curl relaxer formulations, as well as indicating utility in other high pH formulations such as permanent wave products, and the like.

EXAMPLE 44–48 AND CONTROLS E–H

FILM PROPERTIES

These examples demonstrate that the partially hydrolyzed, poly(N-acyl alkylenimines), and derivatives thereof, have desirable film properties. The properties of such films change qualitatively depending upon the mositure content absorbed in the film. Generally, at ambient such films are glossy, smooth and highly deformable. In contrast, cellulosic polymers used in personal care, such as $L_{MW}$QNHEC and HEC are only moderately glossy and have a rougher surface due to fibers. Noncellulosics usable in personal care, such as ES-225, are very glossy and smooth but brittle under the same conditions.

The glossiness provided by such polymers, using the previously described procedure, are set forth in Table 6.

TABLE 6
FILM GLOSS RATINGS

| Example | Polymer | Gloss Readings 20° | 60° |
|---|---|---|---|
| 44 | Example 8 | 5.1[a] | 2.8[a] |
| 45 | Example 17 | 18.0 | 8.7 |
| 46 | Example 19 | 27.6 | 5.3 |
| 47 | Example 20 | 20.3 | 6.1 |
| 48 | Example 21 | 23.1 | 3.7 |
| E | ES-225 | 26.3 | 5.0 |
| F | GAF-937 | 20.1 | 5.0 |
| G | L$_{MW}$QNHEC | 14.2 | 3.5 |
| H | HEC | 10.3 | 2.8 |

[a] low gloss attributed to high salt content in polymer.

The results demonstrate that partially hydrolyzed, poly(N-acyl alkylenimine) provide equivalent to superior gloss readings as compared to commercially available, personal care polymers.

EXAMPLES 49–51 AND CONTROLS I-J

HUMECTANCY

In these examples, the hygroscopicities of the specified partially hydrolyzed, poly(N-propionyl ethylenimines) are measured and compared with commercially available, personal care polymers, using the previously described procedures, with the results set forth in Table 7.

TABLE 7
EQUILIBRIUM MOISTURE CONTENT

| Example | Polymer | Moisture Retention (wt. %) 35% RH | 68% RH | 78% RH |
|---|---|---|---|---|
| 49 | Example 1 | 6.8 | 18.9 | 29.3 |
| 50 | Example 2 | 6.7 | 18.3 | 27.6 |
| 51 | Example 3 | 7.1 | 18.2 | 28.9 |
| I | ES-225 | 2 | 3 | 6.5 |
| J | HEC | 5 | 13 | 18 |

The results demonstrate partially hydrolyzed, poly(N-acyl alkylenimines) exhibit significant hygroscopicity, indicating utility in personal care formulations designed ot improve water retention, i.e., humectants.

EXAMPLES 52–55 AND CONTROL K

SUBSTANTIVITY

In these examples, the substantivities of the partially hydrolyzed, poly(N-propionyl ethylenimines) produced in Examples 1–3 are analyzed.

Electrokinetic analysis, following procedures as described in Goddard et al. *Proceedings of the 15th I.F.S.C.C. Congress*, Volume 1, page 79 (1984), of such partially hydrolyzed, poly(N-acyl alkylenimines) indicates that such polymers provide substantivity due to cationic polymer structure attraction to the negatively charged keratinous surface of the substrate.

The retention of partially hydrolyzed, poly(N-acyl alkylenimines) on hair tresses, prepared and tested using the previously described procedures, also provides evidence of substantivity. Hair tresses and curls are prepared, through application of the specified polymer solutions for one minute with or without rinsing for 30 seconds in running deionized water, and tested with the results set forth in Table 8.

TABLE 8
CURL RETENTION AND EVALUATION

| Example | Polymer | pH | Curl Length, mm (% of control)[a] Initial | After 30' | After 60' | Feel | Appearance |
|---|---|---|---|---|---|---|---|
| 52 | Ex. 9 | 6.75 | 5.8(51%) | 6.9(55%) | 7.5(57%) | Stiff | Shiny |
|  | (Rinsed) |  | 9.3(88%) | 11(92%) | 12(92%) | Mod. Stiff | Mod. Shiny |
| 53 | Ex. 20 | 8.36 | — | — | — | — | — |
|  | (Rinsed) |  | 11.8(104%) | 13.2(106%) | 13.9(106%) | Soft | Same[b] |
| 54 | Ex. 21 | 8.44 | 7.5(66%) | 9.4(75%) | 9.9(76%) | Stiff | Shiny |
|  | (Rinsed) |  | 11.2(99%) | 13.0(104%) | 13.5(103%) | Soft | Same[b] |
| 55 | Ex. 22 | 8.64 | 5.7(50%) | 6.7(54%) | 7.0(53%) | Stiff | Shiny |
|  | (Rinsed) |  | 9.9(88%) | 11.5(92%) | 12.0(92%) | Mod. Stiff | Mod. Shiny |
| K | None |  | 11.3 | 12.5 | 13.1 | — | — |

[a] parenthetical value describes treated curl length as a percentage of curl length of untreated control in water.
[b] same as control These results demonstrate that increased curl retention is provided by all the unrinsed polymer treatments, while substantivity is further established by the stiff feel and shiny appearance of the treated hair. In addition, higher molecular weight, partially hydrolyzed, poly(N-acyl alkylenimines) provide increased curl retention, as well as modified feel and appearance properties, in the rinsed treatments. The results demonstrate substantivity through retention of the partially hydrolyzed, poly(N-acyl alkylenimine) upon application to hair, including after rinse treatment.

EXAMPLE 56

Toxicity

In this example, a blend of poly(N-propionyl ethylenimine), produced following the procedures in Example 8 except that the product is recovered as a 21 weight precent aqueous solution instead of isolating as a dry product and having a salt level of 6.94 wt. %, is evaluated following standard procedures for acute toxicity and primary irritancy analysis. The polymer is of a very low order of acute peroral and percutaneous toxicity, a low order of acute inhalation toxicity by exposure to its vapor generated at ambient temperature, and of minimal irritation to the skin and eye. Such polymers are therefore eminently suited to personal care applications.

We claim:

1. A personal care composition comprising carrier and an effective managing amount of partially hydrolyzed, poly(N-acyl alkylenimine) containing repeating units represented by the structural formula:

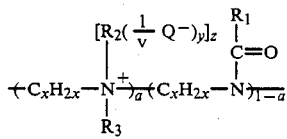

wherein a is from about 1 to about 50 mole percent; and wherein for each repeating unit individually:
Q is an anion;
$R_1$ is hydrogen, alkyl, aryl, aralkyl or alkaryl;
$R_2$ is hydrogen or a hydrocarbyl-containing group;
$R_3$ is hydrogen, oxygen or a hydrocarbyl-containing group;
v is equal to the valence of Q;
x is 2 or 3;
y is 0 or 1; and
z is 0 or 1; provided that:
  (1) when $R_3$ is oxygen than y is 0, $R_2$ is a hydrocarbyl-containing group and z is 1;
  (2) when $R_3$ is not oxygen then y and z are 1; and
  (3) when all z values are 0 then at least one $R_3$ group is a hydrocarbyl-containing group.

2. The composition of claim 1 wherein all $R_2$ and $R_3$ are hydrogen.

3. The composition of claim 1 wherein Q represents a mixture of anions.

4. The composition of claim 1 wherein at least one $R_2$ or $R_3$ is a hydrocarbyl-containing group.

5. The composition of claim 4 wherein at least one hydrocarbyl-conatining group has a cationic or anionic group.

6. The composition of claim 1 containing an effective amount of one or more suitable personal care ingredients sufficient to provide a soap, shampoo, cream, lotion, hair spray, hair or skin conditioner, mousse, antiperspirant, deodorant, hair set, hair wave, hair straightener, make-up, shave cream or gel, after shave lotion or balm.

7. The composition of claim 6 wherein said personal care ingredient is a surfactant, cleanser, colorant, preservative, moisturizer, pH adjustor, emulsifier, propellant, conditioner, thickener, fragrance, foaming agent, sunscreen, depilatory, flavor, astringent agent, antiseptic, deodorant, antiperspirant, insect repellant, bleach, anti-dandruff agent, adhesive, polish, strengthener, filler, barrier material, other personal care ingredient, or mixtures thereof.

8. The composition of claim 1 wherein:
a is from about 3 to about 30 mole percent;
Q is selected from the group consisting of: halides, phosphites, phosphonates, phosphates nitrates, sulfates, sulfonates, carbonates, carboxylates, or mixtures thereof;
$R_1$ is hydrogen, methyl, ethyl or propyl;
each $R_2$ and $R_3$ is individually hydrogen, alkyl, aryl, alkaryl, aralkyl or alkyloxy which is unsubstituted or substituted with hydroxyl, sulfonato, amino, ammonio, carboxyl, carboxylate, or mixtures thereof; and
v is 1 or 2.

9. The composition of claim 1 wherein each $R_1$ is ethyl and each x is 2, providing the poly(N-propionyl ethylenimine) containing repeating units represented by the structural formula:

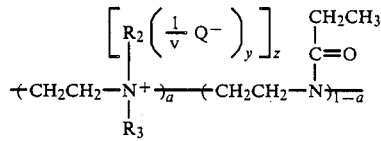

wherein a, Q, $R_2$, $R_3$, v, y and z are as defined in claim 1.

10. The composition of claim 9 wherein:
a is from about 3 to about 30 mole percent;
Q is selected from the group consisting of: halides, phosphites, phosphonates, phosphates, nitrates, sulfates, sulfonates, carbonates, carboxylates, or mixtures thereof;
each $R_2$ and $R_3$ is individually hydrogen, alkyl, aryl, alkaryl, aralkyl or alkyloxy which is unsubstituted or substituted with hydroxyl, sulfonato, amino, ammonio, carboxyl, carboxylate, or mixtures thereof; and
v is 1 or 2.

11. The composition of claim 10 wherein:
a is about 12 mole percent;
Q is chloride, propionate, or mixtures thereof;
each $R_2$ and $R_3$ is individually hydrogen, 2-hydroxy-3-(trimethylammonio)propyl, 2-hydroxy-3-(dimethyldodecylammonio)propyl, 2-hydroxy-3-sulfonatopropyl, 2,3-dihydroxypropyl, or mixtures thereof; and
v is 1.

12. A process for producing a personal care composition which comprises providing a carrier with an effective managing amount of partially hydrolyzed, poly(N-acyl alkylenimine) containing repeating units represented by the structural formula:

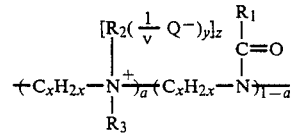

wherein a is from about 1 to about 50 mole percent; and wherein for each repeating unit individually:
Q is an anion;
$R_1$ is hydrogen, alkyl, aryl, aralkyl or alkaryl;
$R_2$ is hydrogen or a hydrocarbyl-containing group;
$R_3$ is hydrogen, oxygen or a hydrocarbyl-containing group;
v is equal to the valence of Q;
x is 2 or 3;
y is 0 is 1; and
z is 0 or 1; provided that:
  (1) when $R_3$ is oxygen then y is 0, $R_2$ is a hydrocarbyl-containing group and z is 1;
  (2) when $R_3$ is not oxygen then y and z are 1; and
  (3) when all z values are 0 then at least one $R_3$ group is a hydrocarbyl-containing group.

13. The process of claim 12 wherein:
a is from about 3 to about 30 mole percent;
Q is selected from the group consisting of: halides, phosphites, phosphonates, phosphates, nitrates, sulfates, sulfonates, carbonates, carboxylates, or mixtures thereof;
each $R_2$ and $R_3$ is individually hydrogen, alkyl, aryl, alkaryl, aralkyl or alkyloxy which is unsubstituted or substituted with hydroxyl, sulfonato, amino, ammonio, carboxyl, carboxylate, or mixtures thereof; and v is 1 or 2.

14. The process of claim 13 wherein each $R_1$ is ethyl and each x value is 2 providing the poly(N-propionyl ethylenimine) containing repeating units represented by the structural formula:

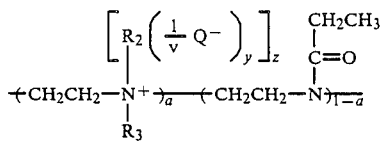

wherein a, Q, $R_2$, $R_3$, v, y and z are as defined in claim 12.

15. The process of claim 14 wherein:
a is about 12 mole percent;
Q is chloride, propionate, or mixtures thereof;
each $R_2$ and $R_3$ is individually hydrogen, 2-hydroxy-3-(trimethylammonio)propyl, 2-hydroxy-3-(dimethyldodecylammonio)propyl, 2-hydroxy-3-sulfonatopropyl, 2,3-dihydroxypropyl, or mixtures thereof; and
v is 1.

16. A process for managing keratinous substrate comprising applying to said substrate an effective managing amount of partially hydrolyzed, poly(N-acyl alkylenimine) containing repeating units represented by the structural formula:

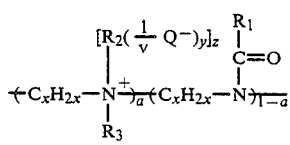

wherein a is from about 1 to about 50 mole percent; and wherein for each repeating unit individually: Q is an anion;
$R_1$ is hydrogen, alkyl, aryl, aralkyl or alkaryl;
$R_2$ is hydrogen or a hydrocarbyl-containing group;
$R_3$ is hydrogen, oxygen or a hydrocarbyl-containing group;
v is equal to the valence of Q;
x is 2 or 3;
y is 0 or 1 and
z is 0 or 1; provided that:
(1) when $R_3$ is oxygen than y is 0, $R_2$ is a hydrocarbyl-containing group and z is 1;
(2) when $R_3$ is not oxygen then y and z are 1; and
(3) when all z values are 0 then at least one $R_3$ group is a hydrocarbyl-containing group.

17. The process of claim 16 wherein:
a is from about 3 to about 30 mole percent;
Q is selected from the group consisting of: halides, phosphites, phosphonates, phosphates, nitrates, sulfates, sulfonates, carbonates, carboxylates, or mixtures thereof;
each $R_2$ and $R_3$ is individually hydrogen, alkyl, aryl, alkaryl, aralkyl or alkyloxy which is unsubstituted or substituted with hydroxyl, sulfonato, amino, ammonio, carboxyl, carboxylate, or mixtures thereof; and
v is 1 or 2.

18. The process of claim 17 wherein each $R_1$ is ethyl and each x value is 2 providing the poly(N-propionyl ethylenimine) containing repeating units represented by the structural formula:

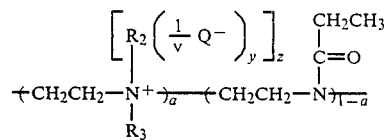

wherein a, Q, $R_1$, v, y and z are as defined in claim 16.

19. The process of claim 18 wherein:
a is about 12 mole percent;
Q is chloride, propionate, or mixtures thereof;
each $R_2$ and $R_3$ is individually hydrogen, 2-hydroxy-3-(trimethylammonio)propyl, 2-hydroxy-3-(dimethyldodecylammonio)propyl, 2-hydroxy-3-sulfonatopropyl, 2,3-dihydroxypropyl, or mixtures thereof; and
v is 1.

* * * * *